United States Patent
Golds et al.

(10) Patent No.: US 7,186,263 B2
(45) Date of Patent: *Mar. 6, 2007

(54) MESH GRAFT AND STENT FOR INCREASED FLEXIBILITY

(75) Inventors: Ellen Golds, Hastings-on-Hudson, NY (US); David Tseng, Santa Rosa, CA (US); Jeff Boatman, Lincoln Park, NJ (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/716,639

(22) Filed: Nov. 19, 2003

(65) Prior Publication Data

US 2004/0162603 A1 Aug. 19, 2004

Related U.S. Application Data

(63) Continuation of application No. 10/716,639, filed on Nov. 19, 2003, which is a continuation of application No. 09/571,530, filed on May 16, 2000, now Pat. No. 6,673,103.

(51) Int. Cl.
*A61F 2/06* (2006.01)
(52) U.S. Cl. .................................... 623/1.13
(58) Field of Classification Search ........ 623/1.1–1.16, 623/1.22, 1.32, 1.36
See application file for complete search history.

(56) References Cited

U.S. PATENT DOCUMENTS

| 4,731,073 | A | * | 3/1988 | Robinson ............... 623/1.44 |
|---|---|---|---|---|
| 4,776,337 | A | | 10/1988 | Palmaz |
| 4,925,710 | A | | 5/1990 | Buck |
| 5,123,917 | A | | 6/1992 | Lee |
| 5,151,165 | A | | 9/1992 | Huynh |
| 5,282,823 | A | | 2/1994 | Schwartz et al. |
| 5,282,824 | A | | 2/1994 | Gianturco |
| 5,389,106 | A | | 2/1995 | Tower |
| 5,466,509 | A | | 11/1995 | Kowligi et al. |
| 5,507,771 | A | | 4/1996 | Gianturco |
| 5,549,663 | A | | 8/1996 | Cottone, Jr. |
| 5,562,697 | A | | 10/1996 | Christiansen |
| 5,562,728 | A | | 10/1996 | Lazarus et al. |

(Continued)

FOREIGN PATENT DOCUMENTS

EP 0689805 A2 1/1996

(Continued)

OTHER PUBLICATIONS

Lyne et al., "Partial encapsulation of stents" Pub. Date: Oct. 18, 2001, USPAP, Pub. No.: US2001/032009.

*Primary Examiner*—(Jackie) Tan-Uyen T. Ho
(74) *Attorney, Agent, or Firm*—Hoffmann & Baron LLP

(57) ABSTRACT

A composite stent-graft tubular prosthesis includes an inner PTFE tubular structure, an outer PTFE tubular structure positioned about the inner PTFE tubular structure and a diametrically deformable stent interposed between the inner and outer PTFE tubular structures. The interposed stent is formed from an elongate wire helically wound with a plurality of longitudinally spaced turns into an open configuration. Each of the turns includes successive aligned upper and lower wave-like peaks. Selective ones of said upper and lower peaks are exposed exteriorly of the outer PTFE structure to render the composite prosthesis longitudinally flexible.

8 Claims, 6 Drawing Sheets

U.S. PATENT DOCUMENTS

| | | |
|---|---|---|
| 5,591,195 A | 1/1997 | Taheri et al. |
| 5,620,763 A | 4/1997 | House et al. |
| 5,628,788 A | 5/1997 | Pinchuk |
| 5,653,697 A | 8/1997 | Quiachon et al. |
| 5,674,241 A | 10/1997 | Bley et al. |
| 5,700,285 A | 12/1997 | Myers et al. |
| 5,713,917 A | 2/1998 | Leoharft |
| 5,718,973 A | 2/1998 | Lewis et al. |
| 5,735,892 A | 4/1998 | Myers et al. |
| 5,749,880 A | 5/1998 | Banas et al. |
| 5,782,904 A | 7/1998 | White et al. |
| 5,810,870 A | 9/1998 | Myers et al. |
| 5,824,037 A | 10/1998 | Fogarty et al. |
| 5,925,074 A | 7/1999 | Gingras et al. |
| 5,925,075 A | 7/1999 | Myers et al. |
| 6,042,605 A | 3/2000 | Martin et al. |
| 6,139,573 A | 10/2000 | Sogard et al. |
| 6,398,803 B1 | 6/2002 | Layne et al. |

FOREIGN PATENT DOCUMENTS

| | | |
|---|---|---|
| EP | 0893108 A2 | 1/1999 |
| WO | WO 95/05132 | 2/1995 |
| WO | WO 95/05555 | 2/1995 |
| WO | WO 96/28115 | 9/1996 |
| WO | WO 98/00090 | 1/1998 |
| WO | WO 98/26731 | 6/1998 |

* cited by examiner

MESH GRAFT AND STENT FOR INCREASED FLEXIBILITY

CROSS REFERENCE TO RELATED APPLICATION

This application is a continuation of and claims priority to Ser. No. 10/716,639, filed Nov. 19, 2003, which is a continuation of Ser. No. 09/571,530 filed May 16, 2000 now U.S. Pat. No. 6,673,103, the contents of which are incorporated herein by reference.

FIELD OF THE INVENTION

The present invention relates generally to an implantable prosthesis used to repair or replace a body lumen. More particularly, the present invention relates to an endoluminal prosthesis including a stent and ePTFE graft composite device offering increased compliance and flexibility.

BACKGROUND OF THE INVENTION

An endoluminal prosthesis is a medical device commonly known to be used in the treatment of diseased blood vessels. An endoluminal prosthesis is typically used to repair, replace, or otherwise correct a damaged blood vessel. An artery or vein may be diseased in a variety of different ways. The prosthesis may therefore be used to prevent or treat a wide variety of defects such as stenosis of the vessel, thrombosis, occlusion, or an aneurysm.

One type of endoluminal prosthesis used in the repair of diseases in various body vessels is a stent. A stent is a generally longitudinal tubular device formed of biocompatible material which is useful to open and support various lumens in the body. For example, stents may be used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents are generally open ended and are radially expandable between a generally unexpanded insertion diameter and an expanded implantation diameter which is greater than the unexpanded insertion diameter. Stents are often flexible in configuration, which allows them to be inserted through and conform to tortuous pathways in the blood vessel. The stent is generally inserted in a radially compressed state and expanded either through a self-expanding mechanism, or through the use of balloon catheters.

A graft is another type of endoluminal prosthesis which is used to repair and replace various body vessels. Whereas a stent provides structural support to hold a damaged vessel open, a graft provides an artificial lumen through which blood may flow. Grafts are tubular devices which may be formed of a variety of material, including textiles, and non-textile materials. One type of non-textile material particularly suitable for use as an implantable prosthesis is polytetrafluoroethylene (PTFE). PTFE exhibits superior biocompatibility and low thrombogenicity, which makes it particularly useful as vascular graft material in the repair or replacement of blood vessels. In vascular applications, the grafts are manufactured from expanded PTFE (ePTFE) tubes. These tubes have a microporous structure which allows natural tissue ingrowth and cell endothelization once implanted in the vascular system. This contributes to long term healing and patency of the graft.

It is also known to combine a stent and a graft to form a composite medical device. Such a composite medical device provides additional support for blood flow through weakened sections of a blood vessel. In endovascular applications the use of a stent/graft combination is becoming increasingly important because the combination not only effectively allows the passage of blood therethrough, but also ensures the implant will remain open.

Several types of stent/graft inventions are known in the art. U.S. Pat. No. 5,151,105 issued to Kwan-Gett discloses a collapsible textile vessel sleeve with stent members positioned at opposite ends of the sleeve. The device is specifically designed to provide a vessel sleeve that is collapsible to a very small diameter in order that it may be placed in position within the abdominal or thoracic aorta by a catheter via the lumen of the femoral artery. Such a procedure obviates the need for a major surgical intervention, and reduces the risks associated with such a procedure.

Other stent/graft composite devices using a textile fabric are shown in U.S. Pat. No. 5,628,788, to Pinchuck.

As mentioned above, ePTFE may also be used as graft material in stent/graft endoprosthesis. One example of an ePTFE stent/graft composite device is shown in U.S. Pat. No. 5,700,285 issued to Myers, et al. Myers discloses a tubular intraluminal graft in the form of a tubular diametrically adjustable stent having an interior and exterior tubular covering of porous expanded polytetrafluoroethylene. The tubular covering surrounds the stent so that the stent is contained during contraction and expansion in the delivery process.

Stents are effectively used in combination with grafts as the composite endoluminal prosthesis allows blood flow through the vessel created by the graft, while the stent maintains its patency. However, as the graft covers the stent, it has a tendency to reduce the longitudinal flexibility of the composite device. Longitudinal compliance is of particular importance to such stent/graft endoluminal prosthesis as the device must be intraluminally delivered through tortuous pathways of a blood vessel to the implantation site where the stent is expanded. A reduction in longitudinal flexibility makes intraluminal delivery more difficult. Reduction in longitudinal flexibility is particularly evident with stents covered by ePTFE, which is not as compliant or flexible as textile materials.

SUMMARY OF THE INVENTION

It is therefore an object of the present invention to provide an endoluminal prosthesis including a stent covered with a graft providing increased longitudinal flexibility.

It is a further object of the present invention to provide a composite stent/graft providing increased compliance and longitudinal flexibility.

It is a still further object of the present invention to provide a composite stent/graft having the fluid retention features of an ePTFE graft without losing the longitudinal flexibility and compliance of a stent.

In the efficient attainment of these and other objectives, the present invention provides a composite stent-graft tubular prosthesis including an inner PTFE tubular structure, and an outer PTFE tubular structure positioned about the inner PTFE tubular structure. A diametrically deformable stent is interposed between the inner and outer PTFE tubular structure. The interposed stent is formed from an elongate wire helically wound with a plurality of longitudinally spaced turns into an open tubular configuration. Each of the turns include successive upper and lower wave-like peaks wherein selective ones of said upper and lower peaks are exposed exteriorly of the outer PTFE structure.

The present invention may further embody a composite stent-graft tubular prosthesis comprising a first PTFE tubular structure with a diametrically deformable stent positioned over said first PTFE tubular structure. The stent being formed of an elongate helically wound wire formed into an open tubular configuration by a plurality of turns. The helically wound wire includes a plurality of transverse generally wave-like undulations there along defining successive upper and lower peaks. The tubular prosthesis further includes a second PTFE tubular structure positioned over said stent. The second PTFE tubular structure includes a plurality of apertures therethrough, the apertures being aligned with selective ones of said upper and lower peaks of the stent to expose said upper and lower peaks to thereby enhance longitudinal flexibility of said prosthesis.

A method of making a stent-graft luminal prosthesis of the present invention is also disclosed. The method provides for the formation of a first PTFE tubular structure. A stent is positioned over said first PTFE tubular structure, the stent having a tubular configuration formed of a plurality of turns of a helically wound wire, with each of said turns including successive upper and lower wave-like peaks. A second PTFE tubular structure is then formed over said stent, with said second PTFE tubular structure exposing selective ones of said upper and lower wave-like peaks through said second PTFE tubular structure.

DETAILED DESCRIPTION OF THE PREFERRED EMBODIMENTS

The following is a detailed description of the preferred embodiments of the present invention. The description is meant to describe the preferred embodiments, and is not meant to limit the invention in any way.

Figure 1:
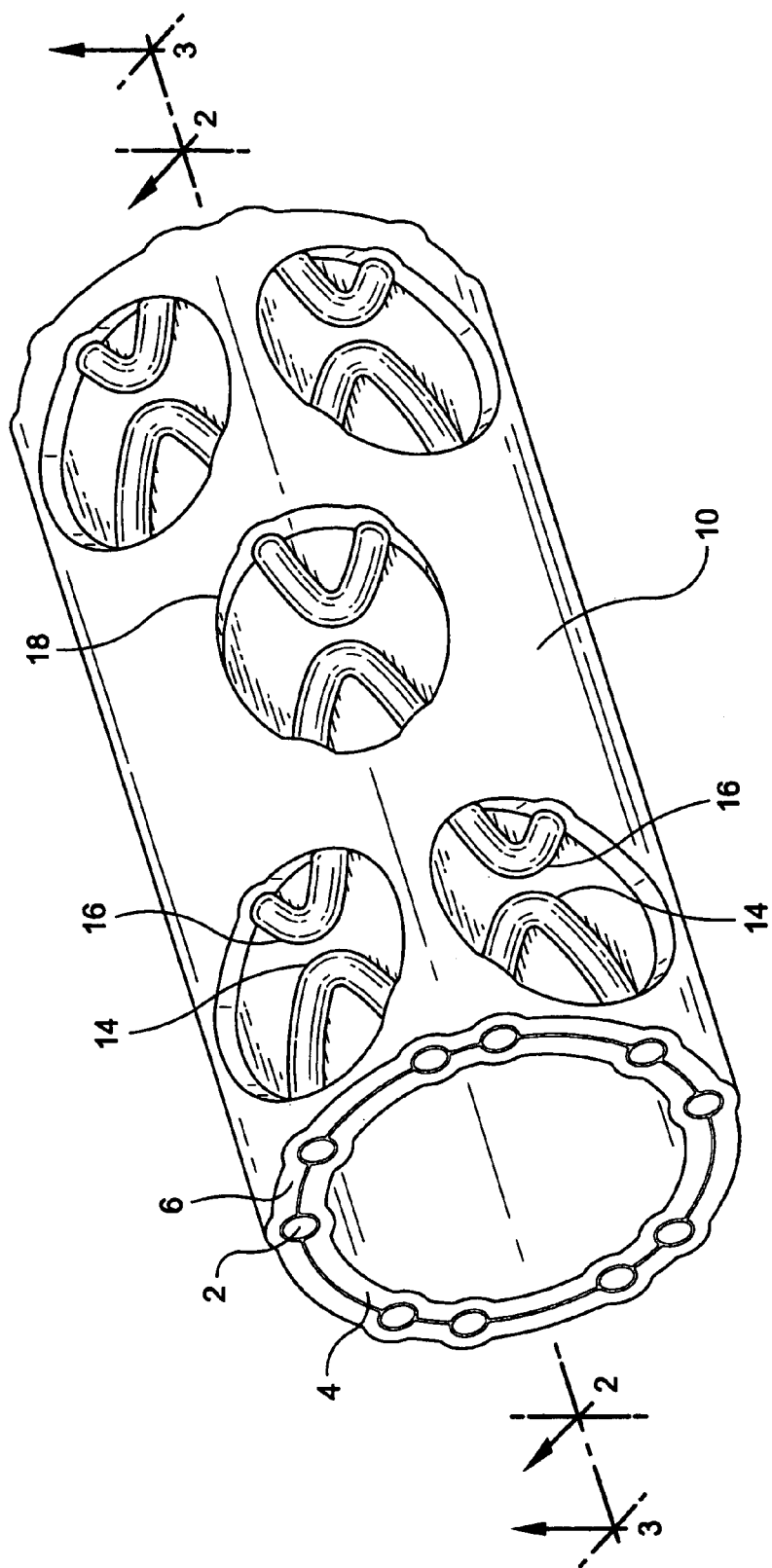
FIG. 1 is a perspective showing, partially in section of a portion of an endoluminal prosthesis of the present invention.

A stent/graft prosthesis 10 of the present invention is shown in FIG. 1. The prosthesis includes a stent 2, an inner tubular layer 4, and an outer tubular layer 6. The stent is positioned between the inner and outer tubular layers.

Figure 6:
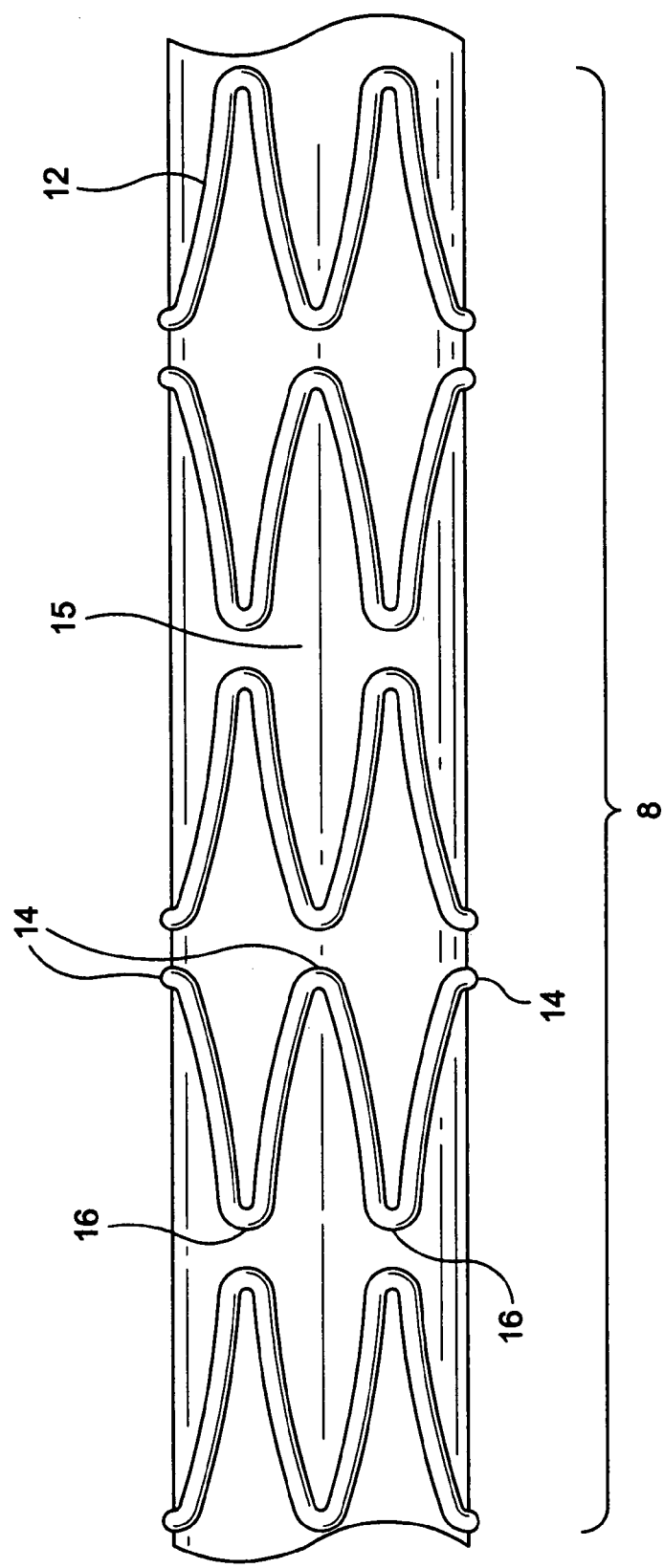
FIG. 6 is a perspective of a stent which may be used in the endoluminal prosthesis of the present invention.

The stent in the present invention is formed from an elongate wire 12 which is helically wound with a plurality of longitudinally spaced turns into an open tubular configuration. As partially shown in FIG. 6, a stent 2 is of the type which is particularly suited for use in the endoluminal prosthesis of the present invention. The stent 2 is an expandable tubular member which may be either of the balloon-expanded or self-expanded type. Stents of this type are typically introduced intraluminally into the body, and expanded at the implantation site. The elongate helically wound wire 12 forming stent 2, defines successive upper wave-like peaks 14, and lower wave-like peaks 16. The wire 12 is wound into a specific configuration where upper peaks 14 are placed adjacent to lower peaks 16 of the next adjacent winding. While the specific configuration of the stent 2 shown herein has been found to be preferable, other stent configurations having open cell expandable construction are within the contemplation of the present invention.

Figure 2:
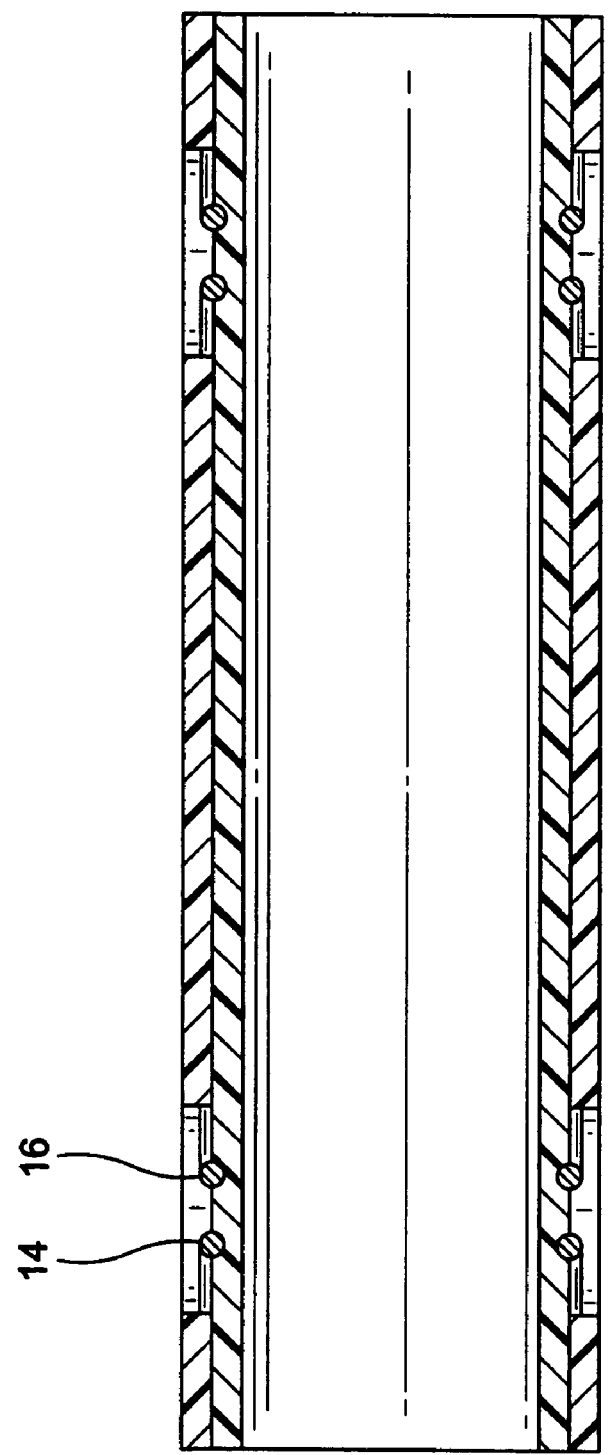
FIG. 2 shows a longitudinal cross-section of the endoluminal prosthesis of FIG. 1 taken through the lines 2—2 thereof.

Referring now to FIGS. 1 and 2, inner and outer tubular layers, 4 and 6 respectively, are shown surrounding stent 2. Layers 4 and 6 are formed of extruded polytetrafluoroethylene (PTFE), as extruded PTFE exhibits superior biocompatibility. Further, PTFE is particularly suitable for vascular applications as it exhibits low thrombogenicity. Tubes of extruded PTFE may also be expanded to form ePTFE tubes. The advantages of the use of ePTFE materials in forming tubular structures for use as vascular grafts are well known.

PTFE may be extruded as a tube or may be extruded as a sheet or film, and subsequently wrapped around a mandrel to form a tubular structure. While ePTFE tubular structures, whether tubes or wrapped ePTFE sheets, exhibit advantageous biophysical compatibility qualities, such structures have a tendency when used in combination with an open stent to reduce the flexibility and longitudinal compliance of the device. This is especially evident where the tubular stent is covered either internally and/or externally with such tubular structures. The present invention is intended to create a stent-graft endoluminal prosthesis exhibiting the beneficial physical properties of ePTFE grafts, without significantly reducing the flexibility of the expandable stent.

In order to increase longitudinal flexibility of stent-graft prosthesis 10, outer PTFE tubular layer 6 is constructed so that it exposes exteriorly the upper wave-like peaks 14, and lower wave-like peaks 16 of stent 2. As mentioned above in a preferred embodiment, the upper wave-like peaks 14 and lower wave-like peaks 16 of the stent are aligned in juxtaposition at various locations along the stent. At such locations the outer tubular layer 6 may be found to have a plurality of apertures 18. These apertures 18 expose the aligned peaks 14 and 16 exteriorly. The inner layer 4 remains continuous particularly underlying apertures 18 so as to maintain a solid tube which functions as a graft.

In the presently described embodiment, all of the stent peaks of a given stent in the prosthesis are exposed. It is contemplated further that only a selected number of aligned peaks may be exposed exteriorly of the endoluminal prosthesis.

The apertures 18 which expose the peaks may be formed into a variety of shapes. As particularly shown in FIG. 1, the apertures 18 are formed as circular holes through which the successive peaks 14 and 16 are exposed. However other aperture configurations may also be employed.

The stent/graft composite device of the present invention is constructed by initially forming a first inner tubular layer 4. As mentioned above, tubular layer 4 maybe formed from an extruded tube or a formed extruded sheet by processes well known in the art. Stent 2 is then positioned over the inner PTFE tubular layer 4. Stent 2 has a tubular configuration formed of a plurality of turns of a helically wound wire, each of said turns including successive upper and lower wave-like peaks. The wound wire is formed such that peaks 14 and 16 are placed in aligned juxtaposition. A second outer PTFE tubular layer 6 is then formed over stent 2. The second outer tubular layer is then modified so as to expose selective aligned upper and lower wave-like peaks through the second PTFE tubular layer 6.

In a preferred embodiment of the present invention, the stent/graft prosthesis includes an open wall stent 12 of tubular construction supported between an inner PTFE tubular layer 4, and an outer PTFE tubular layer 6. The inner PTFE tubular layer 4 may be bonded to the outer PTFE tubular layer through the spaces 15 in the open wall of the stent 2. The bonding may be effectuated with the use of an adhesive, or by adhering the layers together without an adhesive. Bonding of the PTFE layers without an adhesive may take place by such methods as laminating, or sintering of the prosthesis. Furthermore, the stent may be adhered to the inner PTFE tubular layer, the outer PTFE tubular layer, or both. Similarly, such adherence may take place with or without the use of an adhesive.

Once the stent 2 is positioned between layers 4 and 6, a cutting tool (not shown) may be used to expose upper and lower wave-like peaks of the stent exteriorly of the outer PTFE tubular structure. The cutting tool may be used to cut apertures in the outer tubular layer 6 so as to expose the peaks of the stent. Some cutting tools which may be used include a razor blade and a laser. The prosthesis may be sintered prior to exposing the stent peaks, or after said exposure step.

Figure 3:
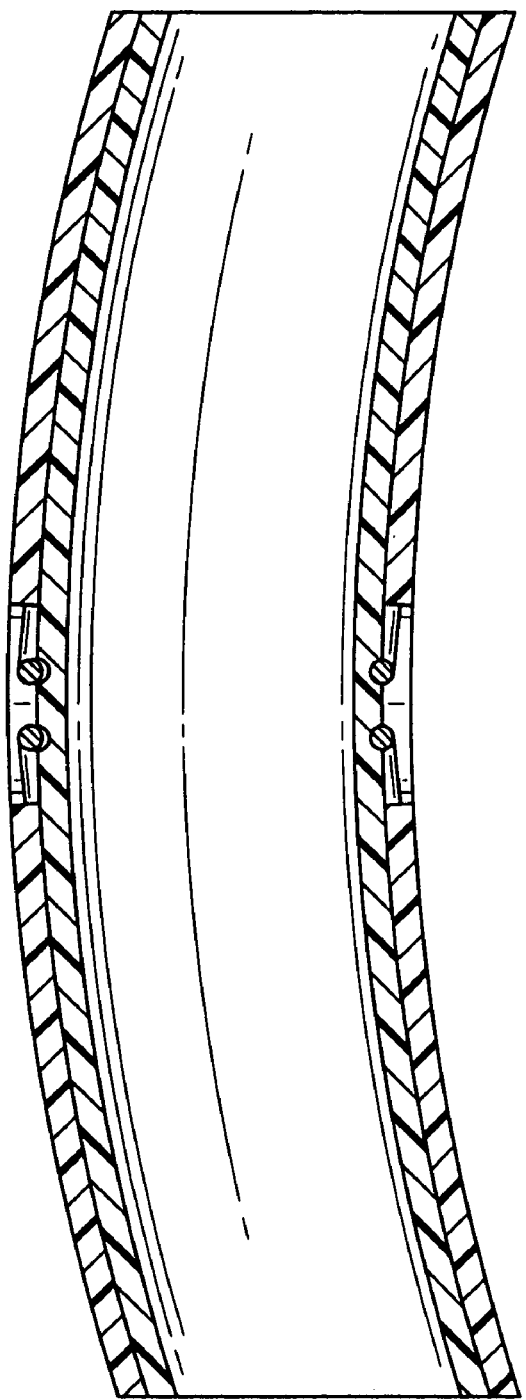
FIG. 3 shows a longitudinal cross-section of the endoluminal prosthesis of FIG. 1 in a flexed position taken through the line 3—3 thereof.
Figure 4:
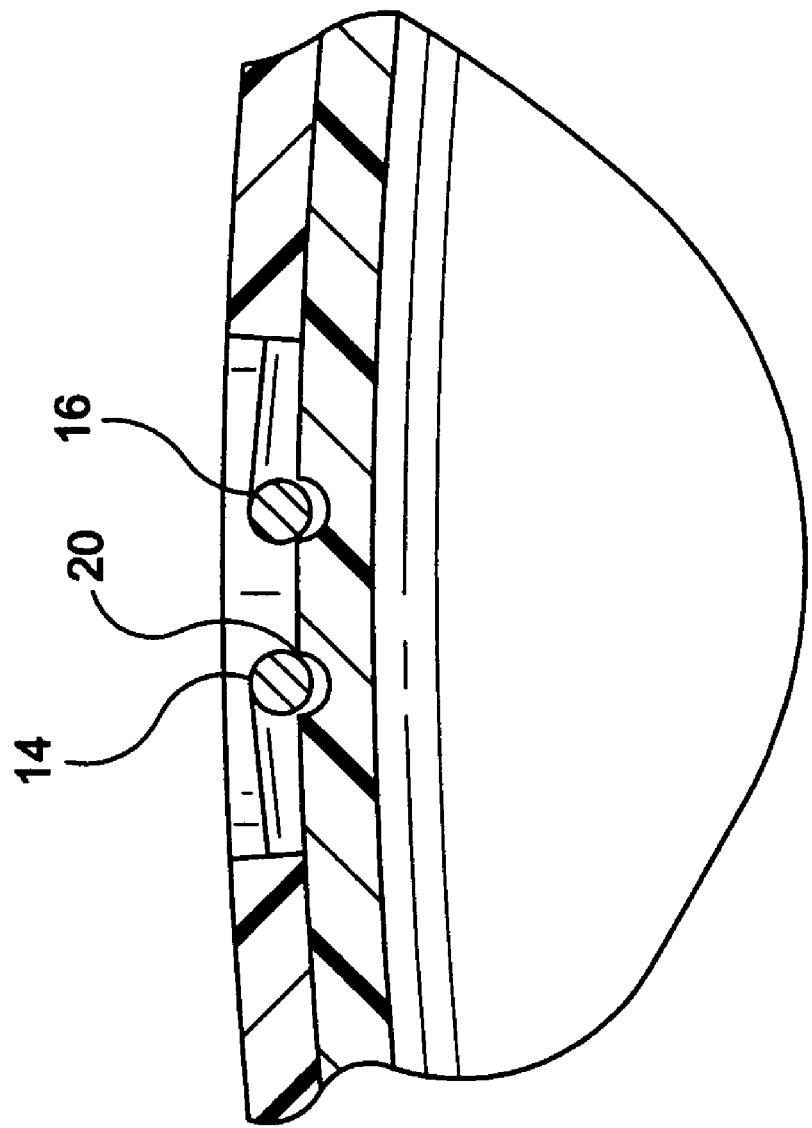
FIG. 4 shows an enlarged cross-section of a portion of the flexed prosthesis of the present invention.

The increased longitudinal flexibility and compliance of the prosthesis may be clearly illustrated with reference to FIGS. 2–4.

As described above the successive upper peaks 14 are juxtaposed with respect to the lower peaks 16. The juxtapositioning of the successive peaks creates a flexion similar to a joint. To further optimize flexibility, the endoluminal prosthesis reduces any movement restriction as between peaks 14 and 16, as the juxtaposed peaks of the stent are exposed exteriorly of the outer PTFE structure. FIG. 4 shows such a longitudinal flexion in the endoluminal prosthesis. Such longitudinal flexion may be the result of intraluminal delivery of the device through the tortuous blood vessel system. As the juxtaposed peaks are exposed exteriorly of the outer PTFE structure, the exposed peaks have a tendency to project externally away from the first tubular structure, creating a space 20 between the stent and the inner tubular structure when longitudinally flexed. The exposure of the peaks enables the stent to exhibit uncovered flexibility as the stent is not restricted from exhibiting movement between the wire windings as would be the case if the stent were completely covered.

Figure 5:
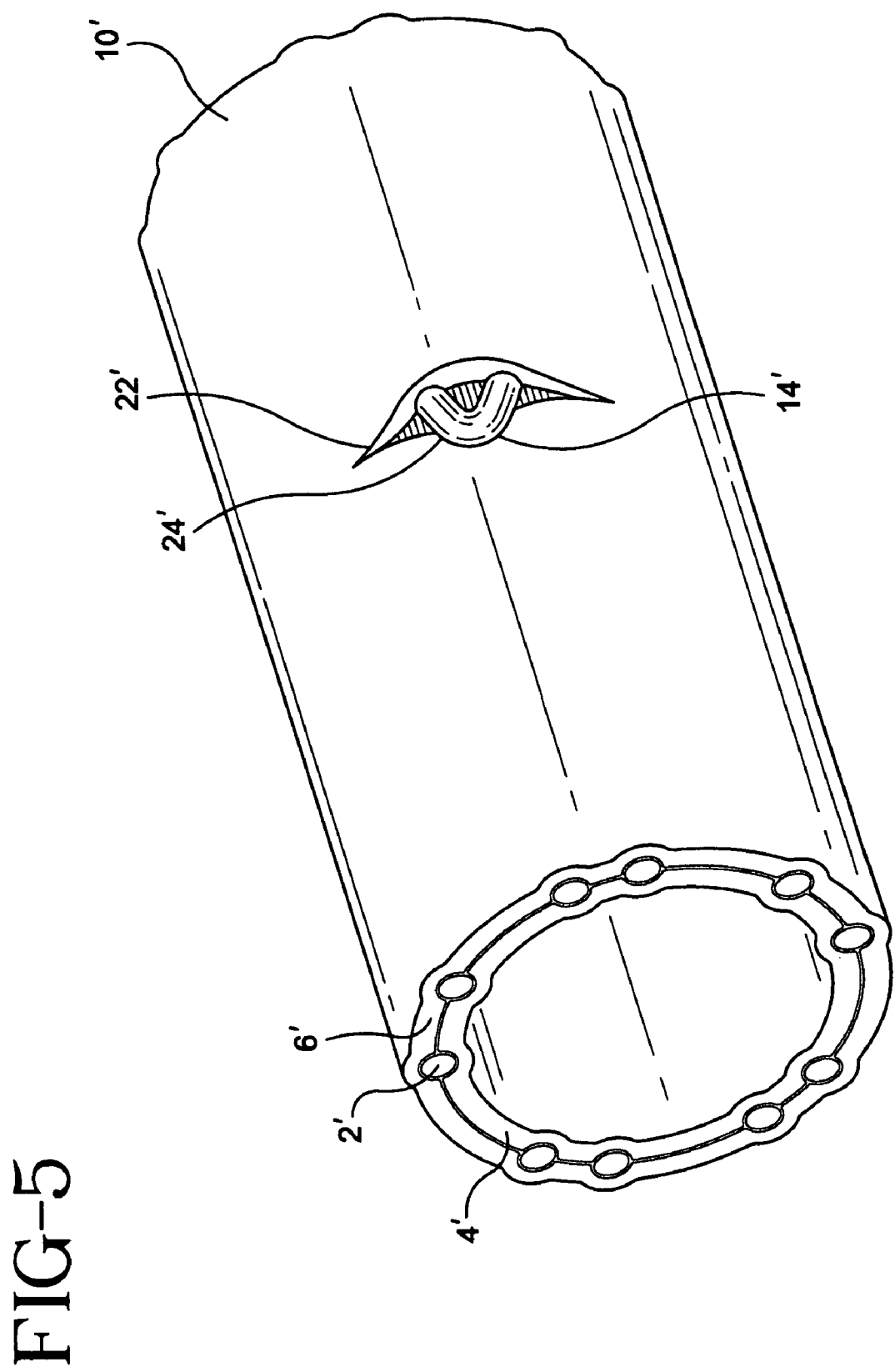
FIG. 5 is a perspective of a further embodiment of the endoluminal prosthesis of the present invention.

As set forth in the above preferred embodiment, longitudinal compliance of the device may be achieved by placing apertures in the outer layer over the aligned peaks of the stent. However, other techniques may be employed to increase the longitudinal compliance of the covered stent. Referring now to FIG. 5, a composite stent/graft prosthesis 10' is shown. Prosthesis 10' is substantially similar to stent/graft prosthesis 10 of FIG. 1, having a stent 2', an inner tubular layer 4' and an outer tubular layer 6'. The stent peaks 14 and 16 may be exteriorly exposed to increase the longitudinal flexibility of the prosthesis 10'.

In the embodiment of FIG. 5, the peaks 14' may be exposed by accessing the stent 2' through the outer layer 6'. A cutting tool (not shown) may be used to cut slits 22' in the outer tubular structure through which the stent peaks 14' are exposed. The stent peaks are subsequently pulled through said slits, and the PTFE comprising the outer tubular structure is subsequently tucked underneath the stent peaks at area 24'. This embodiment provides flexibility in a similar manner because the stent peaks are similarly exposed and the construction allows a full range of motion of the stent peaks. While exposure of only one peak 14' is shown in FIG. 5, it may be appreciated that the exposure of other peaks 14' and 16' may be provided.

What is claimed is:

1. A method of forming a stent-graft prosthesis comprising the step of:
    forming a first PTFE tubular structure;
    positioning a stent over said first PTFE tubular structure, said stent having a tubular configuration formed of a plurality of turns of a helically wound wire, each of said turns including successive upper and lower wave-like peaks;
    forming a second PTFE tubular structure over said stent; and
    exposing selective ones of said upper and lower wave-like peaks through said second PTFE tubular structure, wherein exposing includes placing a plurality of slits through said second PTFE tubular structure at a location aligned with said selective upper and lower peaks of said stent; and extending said upper and lower peaks of said stent through said slits.

2. A method of claim 1 further including the step of adheringly securing said first PTFE tubular stent to said second PTFE tubular structure through spaces between said wound wire.

3. A method of claim 2 wherein said extending step includes:
    lifting said selective upper and lower peaks;
    tucking a portion of said second PTFE tubular structure adjacent said slit, under said upper and lower peaks.

4. A method of claim 2 wherein said placing step includes:
    cutting said slits using a cutting tool.

5. A method of claim 2 wherein said placing step includes:
    laser burning said slits through said second PTFE tubular structure.

6. A method of claim 2 wherein said exposing step includes:
    forming said second PTFE tubular structure with a plurality of apertures, said apertures being at a location adjacent said selective upper and lower peaks.

7. A method of claim 1 wherein said second PTFE tubular structure is sintered prior to said exposing step.

8. A method of claim 1 wherein said second PTFE tubular structure is sintered subsequent to said exposing step.

* * * * *